United States Patent
Koyfman et al.

(10) Patent No.: US 7,481,808 B2
(45) Date of Patent: Jan. 27, 2009

(54) FLEXIBLE ELECTRODE DEVICE AND SURGICAL APPARATUS EQUIPPED WITH SAME

(75) Inventors: Ilya Koyfman, Ringoes, NJ (US); Rajesh Pendekanti, Irwindale, CA (US); Jia Hua Xiao, Plymouth, MN (US)

(73) Assignee: Ethicon, Inc., Somerville, NJ (US)

( * ) Notice: Subject to any disclaimer, the term of this patent is extended or adjusted under 35 U.S.C. 154(b) by 738 days.

(21) Appl. No.: 10/881,692

(22) Filed: Jun. 30, 2004

(65) Prior Publication Data

US 2006/0004353 A1 Jan. 5, 2006

(51) Int. Cl.
*A61B 18/18* (2006.01)
*A61B 5/04* (2006.01)

(52) U.S. Cl. .................. 606/41; 600/372; 600/374
(58) Field of Classification Search ........... 606/1, 606/32–52
See application file for complete search history.

(56) References Cited

U.S. PATENT DOCUMENTS

| | | |
|---|---|---|
| 3,760,812 A | 9/1973 | Timm et al. |
| 3,888,240 A | 6/1975 | Reinhold, Jr. et al. |
| 4,509,535 A | 4/1985 | Bryan |
| 4,709,698 A | 12/1987 | Johnston et al. |
| 5,078,736 A | 1/1992 | Behl |
| 5,455,107 A | 10/1995 | Homma et al. |
| 5,853,411 A | 12/1998 | Whayne et al. |
| 5,891,136 A | 4/1999 | McGee et al. |
| 6,041,260 A | 3/2000 | Stern et al. |
| 6,169,922 B1 | 1/2001 | Alferness et al. |
| 6,231,572 B1 | 5/2001 | Hart et al. |
| 6,315,778 B1 | 11/2001 | Gambale et al. |
| 6,837,886 B2* | 1/2005 | Collins et al. .......... 606/41 |
| 7,255,695 B2* | 8/2007 | Falwell et al. ......... 606/41 |
| 2002/0052601 A1 | 5/2002 | Goldberg et al. |
| 2002/0052612 A1* | 5/2002 | Schmitt et al. ......... 606/151 |

OTHER PUBLICATIONS

Wikipedia, "Zari", printed Aug. 2, 2006 <http://en.wikipedia.org/wiki/Zari> (1 page).
Wikipedia, "Sari", printed Aug. 2, 2006 <http://en.wikipedia.org/wiki/Sari> (7 pages).

* cited by examiner

*Primary Examiner*—Michael Peffley

(57) ABSTRACT

An electrode device adapted for use in medical devices, such as tissue ablation apparatus, includes a sheet of flexible fabric including at least one surface electrode formed as part of the fabric. More particularly, the sheet is made from a plurality of filaments. At least some of the filaments are made at least partially from an electrically conductive material and cooperate so as to form the electrode. The filaments are formed into a plurality of yarns which are interwoven to form the sheet.

16 Claims, 8 Drawing Sheets

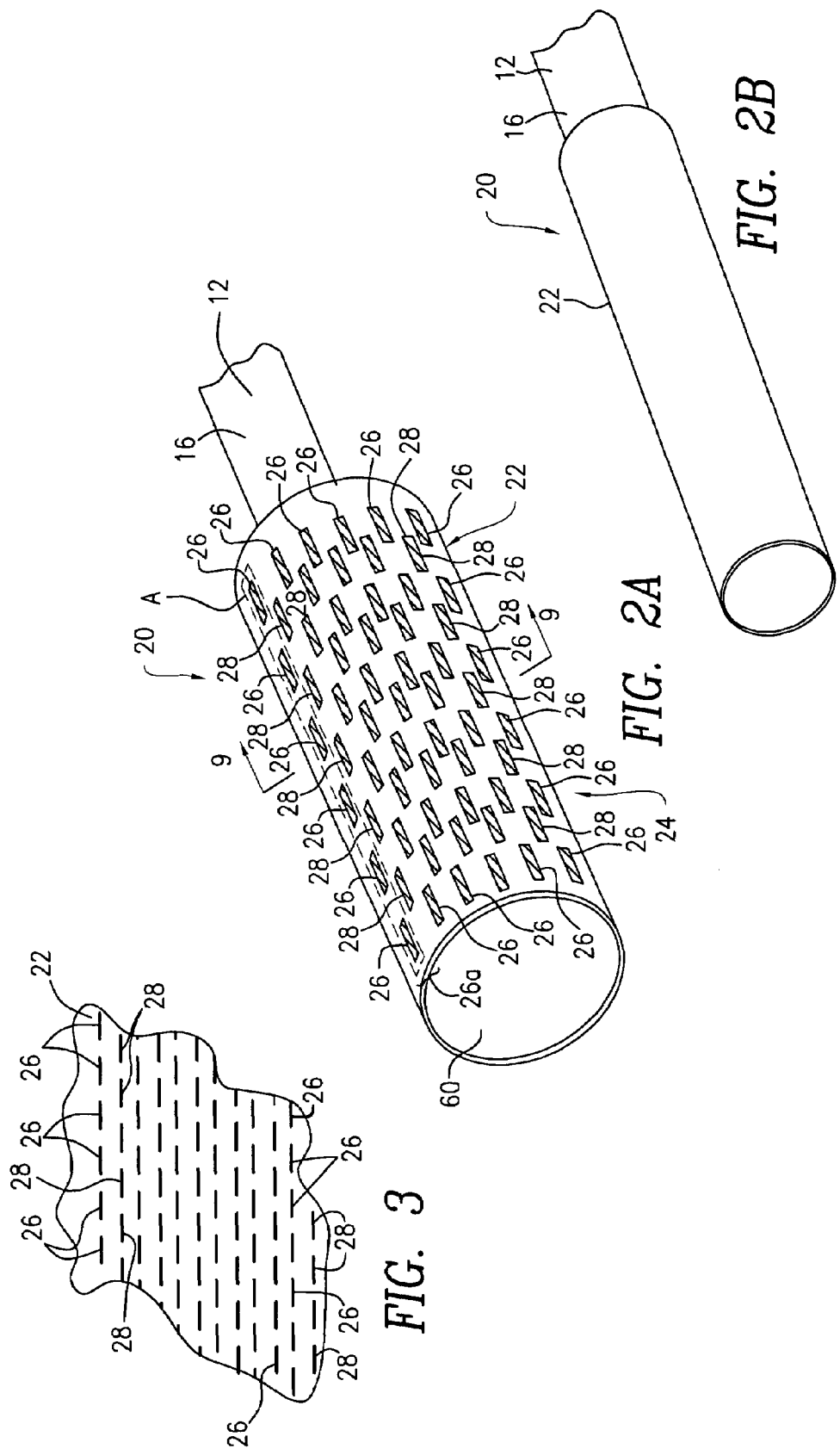

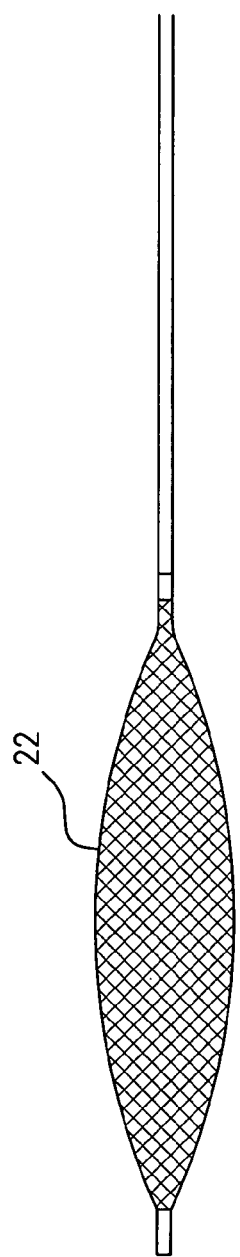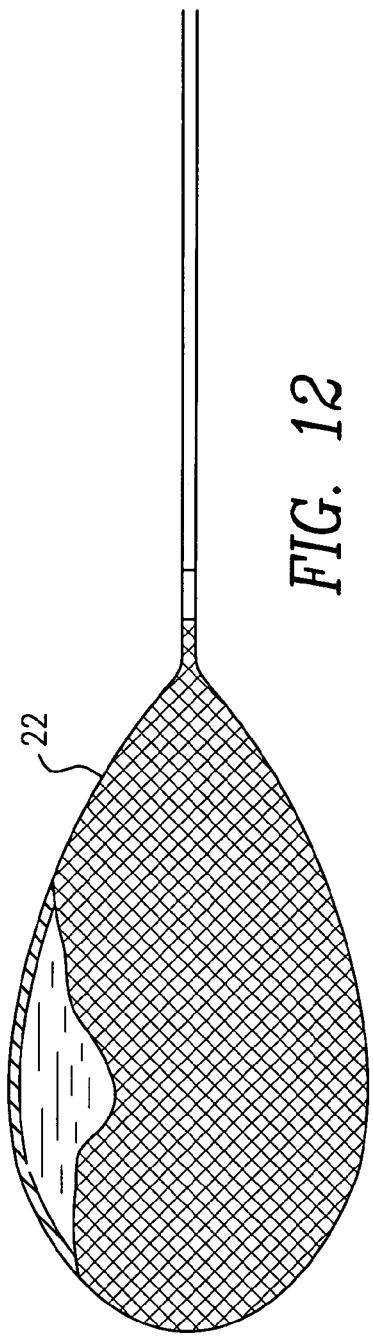

FLEXIBLE ELECTRODE DEVICE AND SURGICAL APPARATUS EQUIPPED WITH SAME

FIELD OF THE INVENTION

The invention relates to medical devices and, more particularly, surgical devices having a flexible, fabric-woven surface electrode structure.

BACKGROUND OF THE INVENTION

Surgical devices have been in use for performing electrosurgical ablation of body tissues. This type of surgical device utilizes electrosurgical energy (e.g., radio frequency (RF) energy) passed between a pair of electrodes to create a high current density which ablate the body tissues.

Efforts have been made in the past to develop flexible electrodes that can be deployed easily at a treatment site. For instance, U.S. Pat. No. 5,891,136 discloses an RF surgical device having an expandable/collapsible electrode structure. While at least some portions of this electrode structure are flexible, it requires a fairly complicated process for forming electrodes thereon and for electrically connecting the electrodes to an external RF energy source.

U.S. Pat. No. 6,231,572 discloses an electrosurgical catheter apparatus having a solid metal electrode which is mounted on an inflatable balloon. While the balloon is expandable for deploying the electrode at a treatment site, the electrode is relatively rigid.

Fabrics patterned with metal strands (e.g., Indian zari sarees and fabrics with bullion emblems) have been available. However, such fabrics are not specifically suitable for medical use.

In the foregoing circumstances, there is a need for an electrosurgical apparatus having flexible electrodes that can be easily deployed at a treatment site and that can be manufactured in a simple, cost-effective manner.

SUMMARY OF THE INVENTION

The present invention overcomes the disadvantages and shortcomings of the prior art discussed above by providing a new and improved electrode device adapted for use in medical apparatus. More particularly, the electrode device includes a sheet of flexible fabric including at least one surface electrode formed as part of the fabric. The sheet is made from a plurality of filaments. At least some of the filaments are made at least partially from an electrically conductive material and cooperate so as to form the electrode. The filaments are formed into a plurality of yarns which are interwoven to form the sheet.

In accordance with another aspect of the present invention, a tissue ablation device is provided. More particularly, the tissue ablation device includes a sheet of flexible fabric including at least one surface electrode formed as part of the fabric. The sheet is made from a plurality of interwoven yarns. At least some of the yarns are made at least partially from an electrically conductive material and cooperate so as to define the electrode. The yarns include a plurality of warp yarns and a plurality of full yarns.

In accordance with yet another aspect of the present invention, a method for making an electrode device adapted for use in medical devices is provided. The method includes the step of providing a plurality of yarns, at least some of which are electrically conductive. A sheet of fabric is formed with the yarns such that at least some of the yarns form at least one electrode. The sheet is then shaped into a predetermined shape.

BRIEF DESCRIPTION OF THE DRAWINGS

For a more complete understanding of the present invention, reference is made to the following detailed description of an exemplary embodiment considered in conjunction with the accompanying drawings, in which:

FIG. 2A is a perspective view of an electrode device of the system shown in FIG. 1, the electrode device being illustrated therein in its expanded configuration;

FIG. 2B is a schematic view of the electrode device of FIG. 2A shown in its collapsed configuration, the electrode device being illustrated therein without its electrodes for the purpose of clarity;

FIG. 3 is a sectional view of a conductive fabric of the electrode device shown in FIG. 2A;

FIG. 11 is a side elevational view of a modified version of the electrode device shown in FIG. 2A, the modified electrode device being shown in its collapsed configuration;

FIG. 12 is a side elevational view of the modified electrode device shown in FIG. 11, the electrode device being shown in its expanded configuration;

DETAILED DESCRIPTION OF THE INVENTION

Although the present invention can be used for many different types of medical devices, it is particularly suitable for use in connection with a tissue ablation device utilizing radio frequency (RF) energy. Accordingly, the present invention will be described hereinafter in connection with such a tissue ablation device. It should be understood, however, that the following description is only meant to be illustrative of the present invention and is not meant to limit the scope of the present invention, which has applicability to other types of medical devices.

Figure 1:
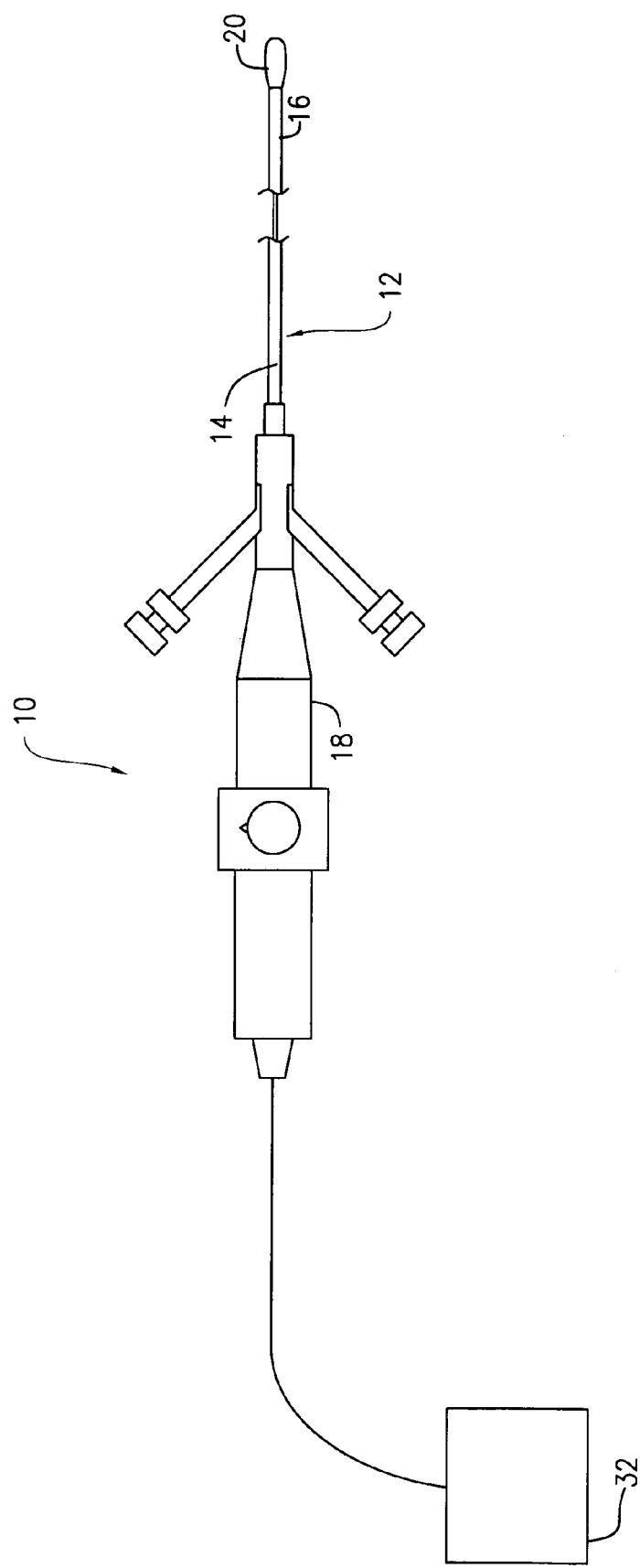
FIG. 1 is a schematic view of an electrosurgical system constructed in accordance with the present invention.

FIG. 1 illustrates a tissue ablation electrosurgical system 10 including a flexible catheter 12 which has a proximal end 14 and a distal end 16. A lumen (not shown) extends through the catheter 12 between the proximal end 14 and the distal end 16. A conventional handle 18 is also located at the proximal end 14 of the catheter 12.

With reference to FIGS. 1 and 2A, the electrosurgical system 10 includes a deployable electrode device 20 constructed in accordance with the present invention. More particularly, the electrode device 20, which is carried at the distal end 16 of the catheter 12, includes a conductive, biocomparable fabric 22 (see also FIG. 3) formed into a predetermined shape and defining an outer layer 24 of the electrode device 20. The conductive fabric 22 has a plurality of surface electrodes 26, 28 formed as an integral part thereof for transmitting radio frequency (RF) energy to body tissues. The electrodes 26 are connected to a common lead wire 30 (see FIG. 4), which in turn is connected to an external RF energy source 32 (see FIG. 1), while the electrodes 28 are connected to a common ground wire 34 (see FIG. 4) such that RF energy can be transmitted from the electrodes 26 to the electrodes 28.

The conductive fabric 22 is formed into a shape or geometry suitable for introduction into a body cavity or conduit (e.g., the atrial chamber of a heart, a uterine cavity, etc.) for ablating tissue therein. For instance, the conductive fabric 22 can be formed into a generally cylindrical or tubular shape (see FIG. 2A) having a suitable size (e.g., about 5 cm in length and about 100 microns in wall thickness). The conductive fabric 22 is preferably elastic such that it is expandable in a generally radial direction from a collapsed configuration (see FIG. 2B), in which it has a sufficiently small diameter or size (e.g., about ¼" in diameter) so as to permit its placement at a desired treatment site in the body of a patient, and an expanded configuration (see FIG. 2A), in which it has a sufficiently large diameter or size (e.g., about 3 inches in diameter) so as to permit efficient tissue ablation. When expanded into its expanded configuration, the conductive fabric 22 is sized and shaped such that it fits in the body cavity or conduit in which the electrode device 20 is placed for performing tissue ablation.

Figure 5:
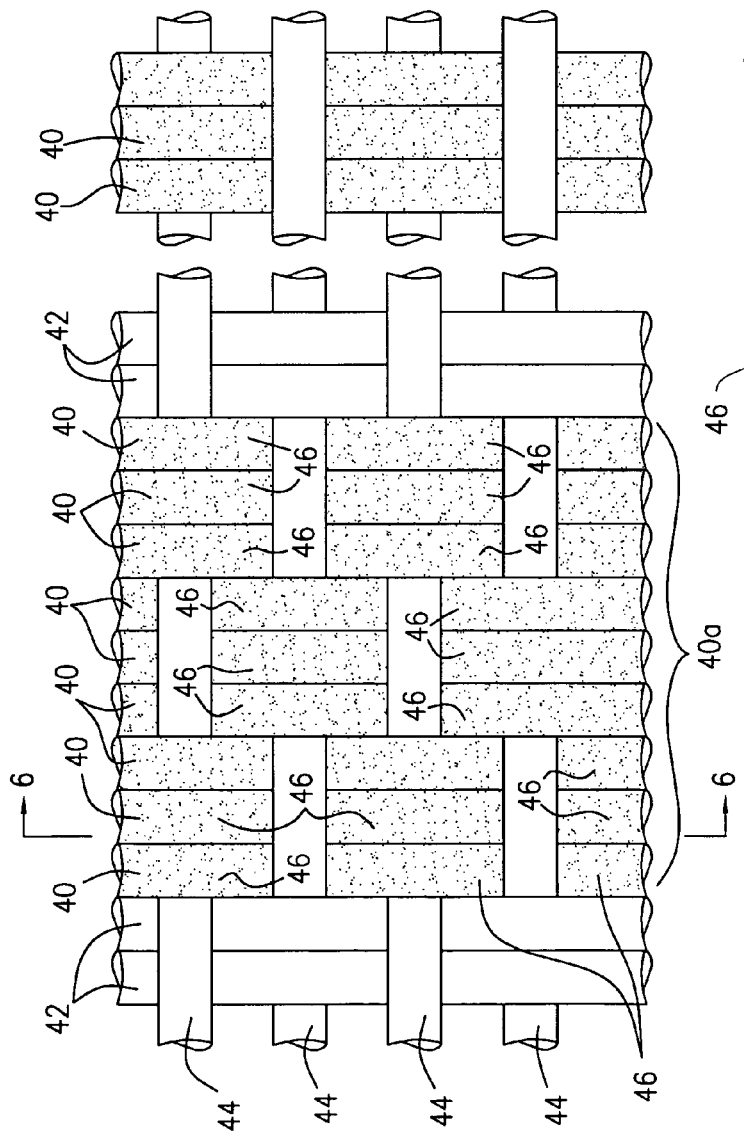
FIG. 5 is an enlarged view of a section of the fabric shown in FIG. 3.
Figure 6:
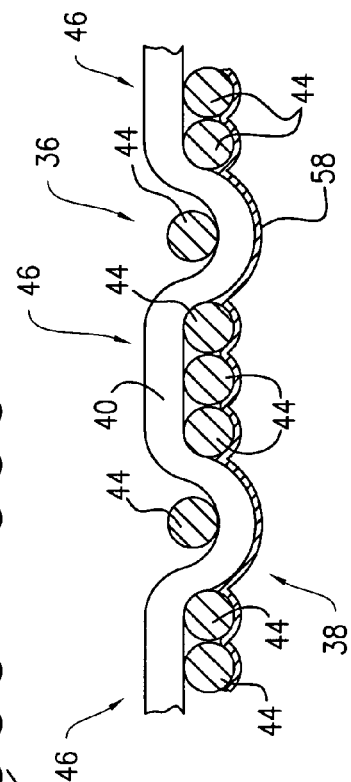
FIG. 6 is a cross-sectional view, taken along section line 6-6 and looking in the direction of the arrows, of the fabric section shown in FIG. 5.

With reference to FIGS. 2A, 5 and 6, the conductive fabric 22, which has an outer surface 36 and an inner surface 38, is made from electrically conductive warp yarns 40 and electrically nonconductive warp yarns 42 woven with nonconductive fill yarns 44 in a conventional manner. The conductive and nonconductive warp yarns 40, 42 extend in a lengthwise direction of the conductive fabric 22, while the nonconductive fill yarns 44 extend in a widthwise direction of the conductive fabric 22. As will be discussed in greater detail hereinbelow, the warp yarns 40, 42 are interwoven with the fill yarns 44 such that segments 46 (see FIGS. 5 and 6) of the conductive warp yarns 40 are exposed in desired patterns and/or shapes on the outer surface 36 of the conductive fabric 22. The exposed segments 46 of the conductive warp yarns 40 define the electrodes 26, 28 of the electrode device 20, each of which is hence an integral, woven part of the conductive fabric 22.

Figure 7:
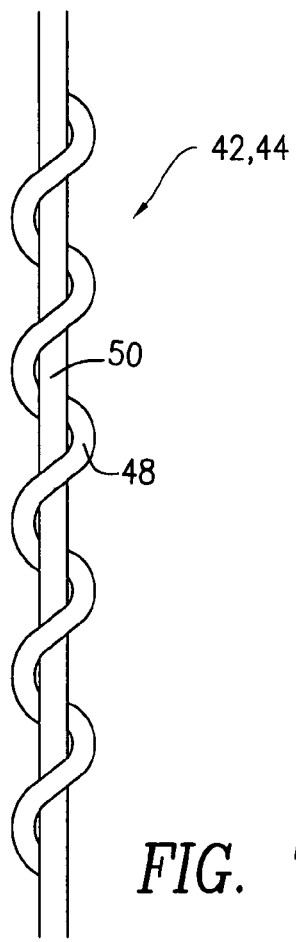
FIG. 7 is an elevational view of a nonconductive yarn utilized in making the fabric of FIG. 3.

Now referring to FIG. 5, while the conductive and nonconductive yarns 40, 42, 44 can be non-elastic, in order to provide the conductive fabric 22 with sufficient elasticity (i.e., to permit expansion and contraction between its collapsed and expanded configurations), they are preferably made to be elastic. For instance, each of the nonconductive warp and fill yarns 42, 44 can be made by helically winding a reinforcement strand 48 (see FIG. 7) about an elastic strand 50 such that the nonconductive yarns 42, 44 are stretchable in an axial direction. The reinforcement strands 48 are provided to reinforce the elastic strands 50 and to limit excessive expansion of the elastic strands 50.

The reinforcement strands 48 of the nonconductive yarns 42, 44 can be made from any suitable conventional natural materials (e.g., silk, cotton, etc.) or synthetic materials (e.g., polyester, nylon, polypropylene, polyethylene, etc.) and can be provided with any suitable size (e.g., 10-200 denier). The elastic strands 50 of the nonconductive yarns 42, 44 can be made from any suitable conventional materials which offer good durability, elasticity and abrasion resistance (e.g., spandex, hytrlel, rubber, etc.). The elastic strands 50 can also be provided with any suitable size (e.g., a 70 denier strand). In one embodiment of the present invention, each nonconductive yarn 42, 44 includes a 50 denier polyester strand 48 wrapped or coiled helically around a 70 denier spandex strand 50.

The elasticity of the nonconductive warp and fill yarns 42, 44 is determined by the number of turns of each reinforcement strand 48 per inch of the corresponding elastic yarn 50 (i.e., turns per inch or "tpi"). While any suitable turns per inch can be used for making the nonconductive warp and fill yarns 42, 44, the nonconductive yarns 42, 44 are provided with preferably about 15-20 tpi, and more preferably about 18 tpi.

Figure 8:
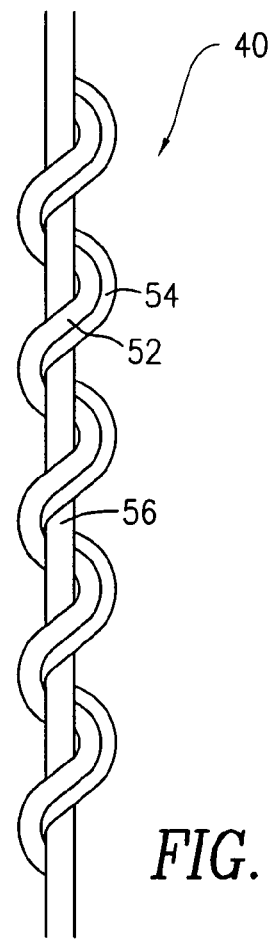
FIG. 8 is an elevational view of a conductive yarn utilized in making the fabric of FIG. 3.

Like the nonconductive warp and fill yarns 42, 44, the conductive warp yarns 40 are made to be elastic so as to provide the conductive fabric 22 with sufficient elasticity. More particularly, each of the conductive warp yarns 40 can include a reinforcement strand 52 and an electrically conductive strand or ribbon 54, both of which are helically wound about an elastic strand 56 (see FIG. 8). The reinforcement strands 52 are provided to reinforce the elastic strands 56 and to limit excessive expansion of the elastic strands 56. The conductive strands 54 wrapping around the elastic strands 56 provide the conductive warp yarns 40 with a good electric conducting property.

The conductive strands 54 of the conductive warp yarns 40 can be made from any suitable electrically conductive materials (e.g., gold, silver, platinum, titanium, Pt—Ir, etc.), while the reinforcement strands 52 of the conductive warp yarns 40 can be made from any suitable natural or synthetic materials, such as cotton, silk, polyester, nylon, polypropylene, etc. The conductive strands 54 and the reinforcement strands 52 can be provided with any suitable sizes. For instance, the conductive strands 54 can have a thickness preferably ranging from about 10 microns to about 100 microns and more preferably of about 50 microns, while the reinforcement strands 52 can be provided with a size of approximately 10-200 denier and, more preferably, about 50 denier. Likewise, the elastic strands 56 of the conductive warp yarns 40 can be made from any suitable conventional materials which offer good durability, elasticity and abrasion resistance (e.g., spandex, hytrel, rubber, etc.). The elastic strands 56 can also be provided with any suitable size (e.g., a 70 denier strand). In one embodiment of the present invention, each conductive warp yarn 40 includes a 50 denier polyester strand 52 and a 10 micron metallic strand. 54 wrapped or coiled around a 70 denier spandex strand 56.

Like the nonconductive warp and fill yarns 42, 44, the elasticity of the conductive warp yarns 40 is determined by the number of turns of the reinforcement and conductive strands 52, 54 per inch of the corresponding elastic yarn 56 (i.e., turns per inch or "tpi"). While any suitable turns per inch can be used for making the conductive warp yarns 40, the conductive yarns 40 can be provided with preferably about 15-20 tpi, and more preferably about 18 tpi.

The conductive and nonconductive warp yarns 40, 42 are interwoven with the nonconductive fill yarns 44 such that the exposed segments 46 of the conductive warp yarns 40 form the electrodes 26, 28 of the electrode device 20. Any conventional weaving method (e.g., tabby weaving methods, jacquard weave methods and methods utilized in the textile industry for making fabrics patterned with metal strands such as bullion emblems and Indian zari sarees) can be utilized for making the conductive fabric 22 using the warp yarns 40, 42 and the fill yarns 44 and for shaping and/or patterning the electrodes 26, 28 on the outer surface 36 of the conductive fabric 22. For instance, a conventional uneven twill weaving method can be used for making the conductive fabric 22 and patterning the surface electrodes 26, 28. By way of example, each of the electrodes 26, 28 is formed by a set of the conductive warp yarns 40 passing under one and over two or more nonconductive fill yarns 44 (see FIGS. 5 and 6) such that the conductive warp yarns 40 are exposed to the outer surface 36 of the conductive fabric 22 to a greater extent than the nonconductive fill yarns 44, forming the electrodes 26, 28 (i.e., the electrodes 26, 28 are formed by the exposed conductive yarn segments 46). Other conventional methods utilized in the textile industry for forming desired fabric patterns and shapes (e.g., a knitting method) can also be utilized for making the conductive fabric 22.

The warp and fill yarns 40, 42, 44 are interwoven together such that the conductive fabric 22 is provided with any suitable weave density, and thickness, so long as the structure and functionality of the electrode device 20 is not compromised. For instance, the conductive fabric 22 can be provided with a warp count ranging from about 180 picks per inch to about 300 picks per inch, while the fill count of the conductive fabric 22 can range preferably from about 30 picks per inch to about 70 picks per inch. More preferably, the conductive fabric 22 can be provided with a warp count of about 240 picks per inch and a fill count of about 50 picks per inch.

Figure 4:
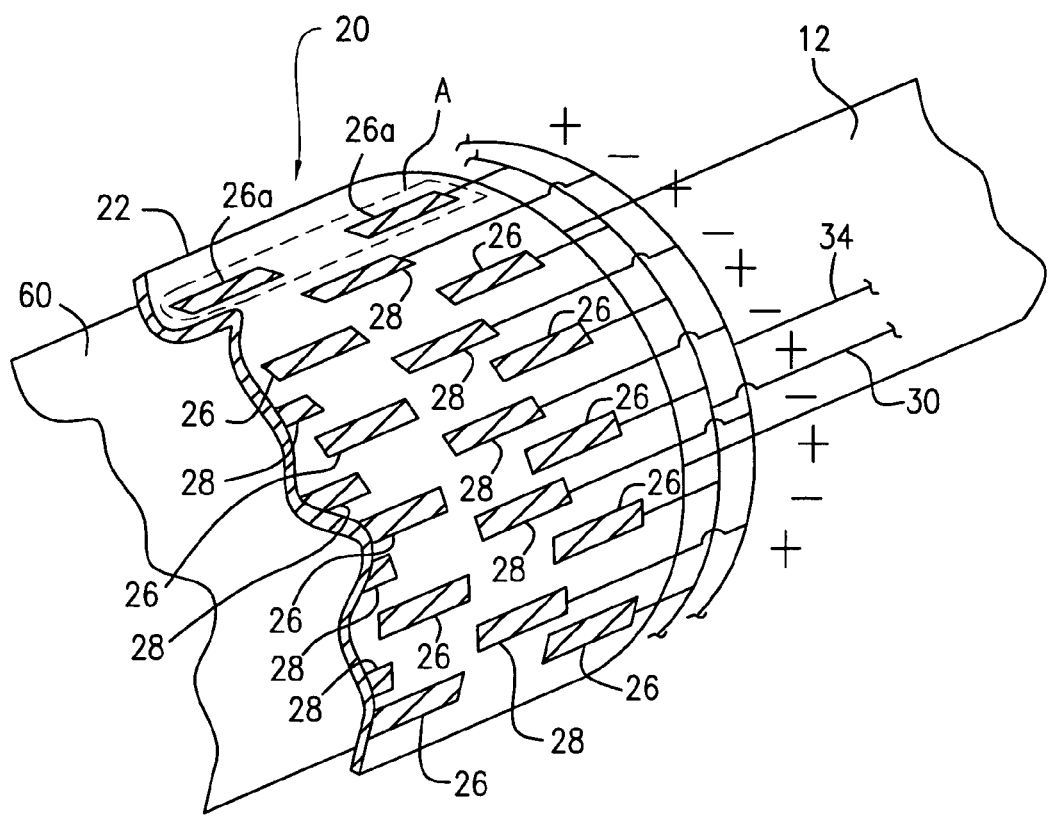
FIG. 4 is a schematic view of a proximal end of the electrode device shown in FIG. 2A.

With reference to FIG. 4, the electrodes 26 are electrically wired to the common lead wire 30, which in turn is connected to the RF energy source 32 (see FIG. 1), while the electrodes 28 are connected to the common ground wire 34 such that RF energy can be transmitted from the electrodes 26 to the electrodes 28. More particularly, because each set or array of the electrodes 26, 28 is formed by a common set of conductive warp yarns 40 (e.g., the electrodes 26a arranged in row A in FIGS. 2A and 4 are formed by a set of conductive warp yarns 40a in FIG. 5), the electrodes 26, 28 in each array are electrically connected to one another. As a result, only one wiring connection is required for each electrode array to electrically connect same to the common lead wire 30 or the common ground wire 34.

With reference to FIGS. 4-6, as discussed above, a set of the conductive warp yarns 40 forms a corresponding array of the electrodes 26, 28. In order to electrically insulate adjacent arrays of electrodes 26, 28, the nonconductive warp yarns 42 are interwoven together with the nonconductive fill yarns 44 between each adjacent pair of electrode arrays (see FIG. 5). The inner surface 38 of the conductive fabric 22 can also be coated with an electrically insulating material 58 for electrical insulation of non-exposed segments of the conductive warp yarns 40.

Figure 9:
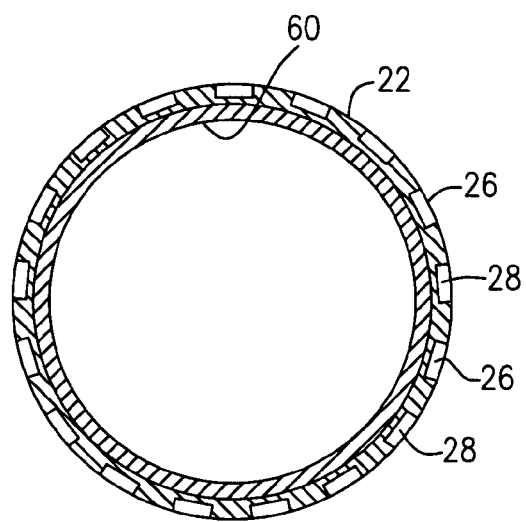
FIG. 9 is a cross-sectional view, taken along section line 9-9 and looking in the direction of the arrows, of the electrode device shown in FIG. 2A.

In order to expand the conductive fabric 22 from its collapsed configuration to its expanded configuration, the electrode device 20 is provided with a balloon 60 (see FIGS. 2A, 4 and 9) connected to the distal end 16 of the catheter 12. The balloon 60, which is mounted within the conductive fabric 22, has a construction and operation similar to those of a balloon of a conventional catheter (e.g., the inflatable balloons disclosed in U.S. Pat. Nos. 5,891,136 and 6,231,572, the disclosures of which are incorporated herein by reference in their entirety). For instance, when fluid (e.g., a saline solution) is injected into the balloon 60 through the lumen of the catheter 12, the balloon 60 expands radially outwardly, thereby causing the conductive fabric 22 to assume its expanded configuration from its collapsed configuration. Alternatively, other types of expanding mechanisms can be utilized instead of the balloon 60.

Figure 10:
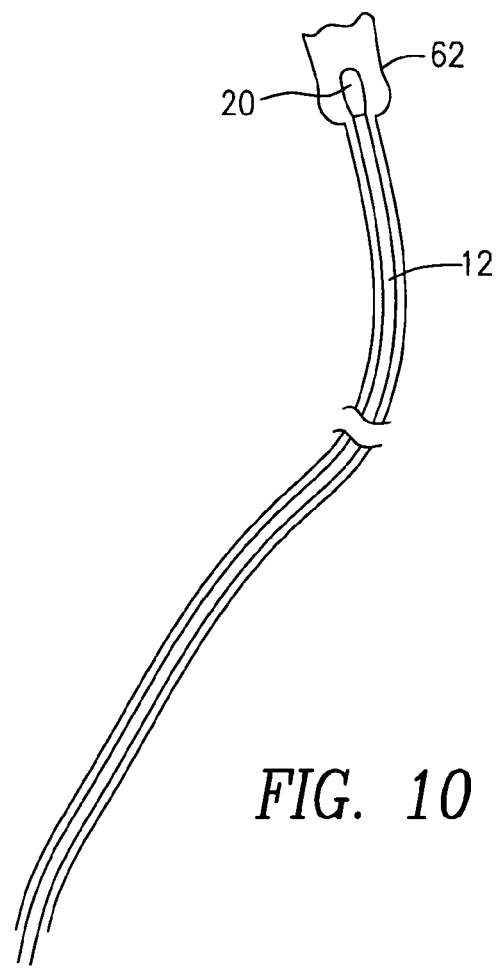
FIG. 10 is a schematic view of the electrosurgical system shown in FIG. 1, illustrating its deployment at a treatment site for performing tissue ablation.

With reference to FIG. 10, in order to perform tissue ablation at a treatment site 62 (e.g., the atrial chamber of a heart, a uterine cavity, etc.), the electrode device 20 is delivered into the body of a patient to the treatment site 62 in its collapsed configuration using a conventional method. For instance, a guide wire and a sheath (not shown) can be use to deliver the electrode device 20 to the treatment site 62. After properly positioning the electrode device 20 at the treatment site 62, the balloon 60 is expanded by introducing fluid thereinto, causing the electrode device 20 to assume its expanded configuration. RF energy is then applied from the RF energy source 32 so as to perform ablation of tissues at the treatment site 62. After the performance of the tissue ablation, the fluid contained in the balloon 60 is withdrawn, thereby causing the electrode device 20 to contract to its collapsed configuration for withdrawal of same from the treatment site 62.

Figure 13:
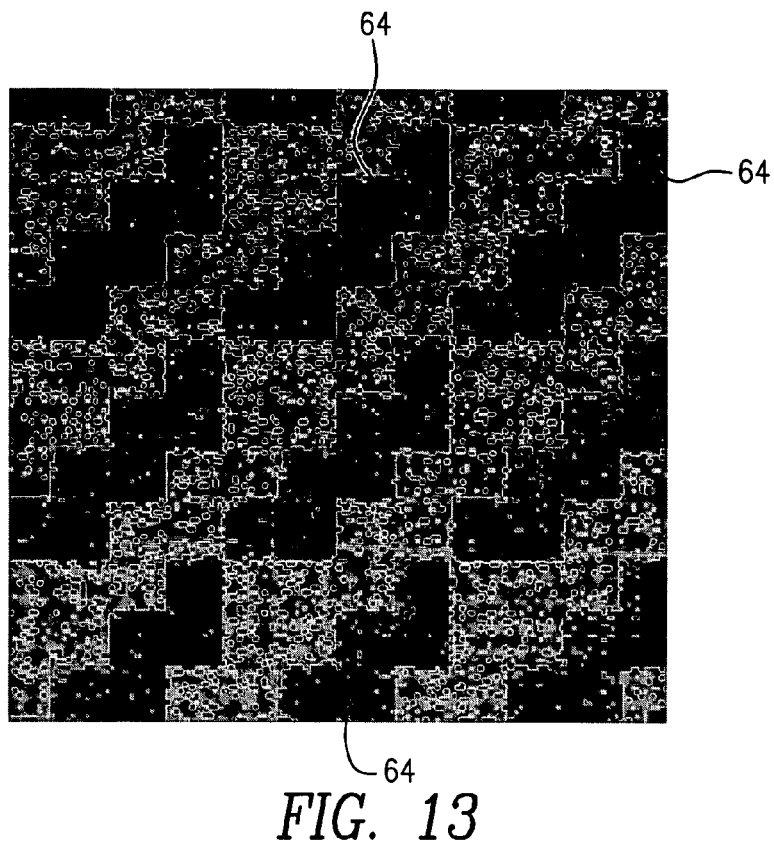
FIG. 13 is a view illustrating an alternate electrode pattern and shape.
Figure 14:
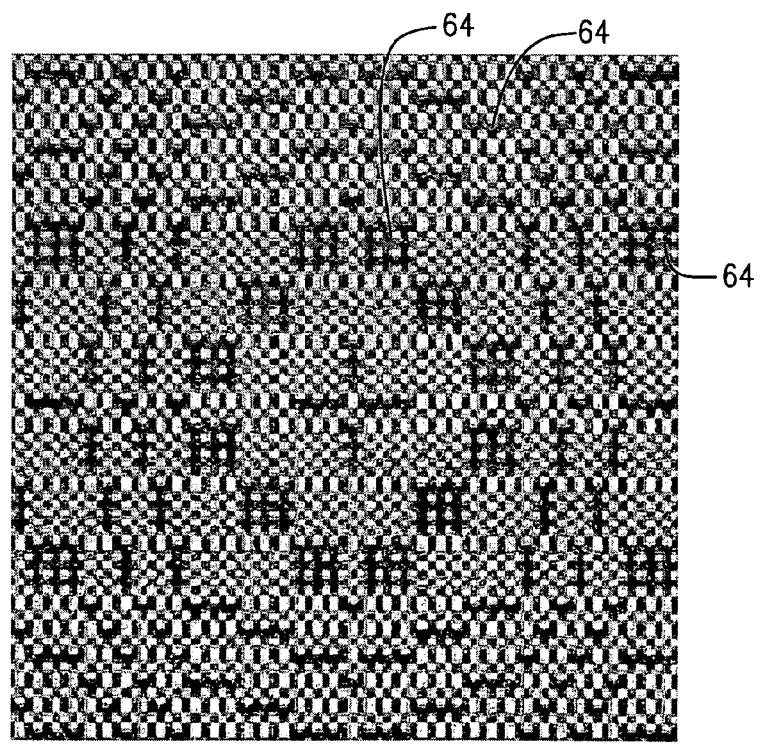
FIG. 14 is a view illustrating another alternate electrode pattern and shape.

It should be appreciated that the present invention provides numerous advantages over the prior art discussed above. For instance, because the electrodes 26, 28 are formed as integrated part of the conductive fabric 22, they are flexible and adapted for easy deployment at a treatment site. Moreover, with the use of a conventional fabric manufacturing process, the electrodes 26, 28 can be easily shaped and patterned on the conductive fabric 22 in any desired manner. For example, FIGS. 13 and 14 illustrate alternate electrode shapes and patterns (represented therein by the dark areas 64) which can be formed easily and cost-effectively. In such circumstances, it is possible to make electrodes having complex patterns/shapes and having large coverage areas. The electrodes 26, 28 can therefore be patterned such that the entire RF energy passing between the electrodes 26, 28 is focused substantially on the lesion area, thereby protecting healthy tissues.

Because the electrodes 26, 28 formed by the same set of the conductive warp yarns 40 are electrically connected to each other, wiring of the electrodes 26, 28 to the RF energy source 32 is rendered relatively simple. That is, only one wiring connection is required to power all electrodes 26, 28 formed by the same set of the conductive yarns 40.

It should be noted that the present invention can have numerous modifications and variations. For instance, the electrode device 20 can be provided with a different mechanism for expanding the conductive fabric 22 from its collapsed configuration to its expanded configuration. By way of example, the electrode device 20 can be equipped with the flexible spine element/sheath arrangement disclosed in U.S. Pat. No. 5,891,136. The conductive fabric 22 can also be constructed such that it is fluid-tight. In such an embodiment, the conductive fabric 22 can functions as a balloon, thereby eliminating the need to provide a separate balloon structure.

The conductive fabric 22 can also be modified in numerous ways. For instance, the elastic strands 50, 56 of the warp yarns 42, 40, respectively, can be textured strands to provide same with elasticity. Alternatively, the warp yarns 42, 40 can be made without the elastic strands 50, 56, respectively, such that only the fill yarns 44 are elastic. In such circumstances, the conductive fabric 22, which is in a tubular shape, is expandable only in a radial direction (i.e., the conductive fabric 22 is not expandable in an axial direction). All of the warp yarns 40, 42 and the fill yarns 44 can also be made without the elastic strands 50, 56 such that the entire conductive fabric 22 is substantially non-elastic. In this configuration, the conductive fabric 22 can be provided with a pleated or folded construction such that it can expand from its folded configuration to its expanded configuration.

The conductive fabric 22 can also be formed into a different shape, depending upon the requirements/needs of the electrode device 20. For instance, the conductive fabric 22 can be formed into an oblong shape and can expand from a collapsed configuration (see FIG. 11) to an expanded configuration (see FIG. 12). The conductive fabric 22 can also be made using processes other than weaving methods. For example, the conductive fabric 22 can be formed as a knitted fabric.

The electrode device 20 of the present invention can be bipolar or monopolar. When used as a monopolar device, all of the electrodes 26, 28 formed on the conductive fabric 22 are wired to the common lead wire 30 for being powered by the RF energy source 32.

The conductive warp yarns 40 can also be modified in numerous ways. For instance, each conductive yarn 40 can be formed entirely of flexible metallic filaments which are twisted with each other. Moreover, each conductive yarn 40 can be formed as a single conductive filament, thread, ribbon or wire. Accordingly, as used herein, the term "yarn" shall denote to include a composite yarn which are made from multiple filaments or threads, as well as a yarn which is constructed entirely of a single filament, thread, ribbon or wire. The conductive yarns 40 can also be formed by a non-conductive yarn deposited or coated with conductive materials.

The conductive yarns 40 can also be formed of three components (i.e., a metallic alloy wire, a silk thread and a gold coating) which are integrated together by a conventional spinning and gilding process to make Indian zari sarees. More particularly, the metallic wire can be made from silver and copper in a desired composition (e.g., 77% silver and 23% copper) and is flattened to a suitable size (e.g., 25 microns in thickness). The silk thread can form the core over which the flattened metallic wire can be wound. The uncoated metallic wire can then be coated with a gold coating by using a conventional electroplating process to give uniform covering with a desired overall gold content (e.g., 0.59%-0.60%).

The present invention can also be used in connection with other medical devices requiring the use of electrodes. For instance, the electrode device 20 of the present invention can be used in conjunction with other surgical instruments. Moreover, the electrode device 20 of the present invention can be used in a device for monitoring electrical signals generated by organs or body tissues (e.g., for sensing electrical activity in a heart).

The conductive fabric 22 can be permanently attached to the balloon 60. Alternatively, the conductive fabric 22 can be removably attached to the balloon 60. In this manner, the conductive fabric 22 can be removed easily from the balloon 60 for disposal and/or replacement with another conductive fabric.

It will be understood that the embodiments described herein are merely exemplary and that a person skilled in the art may make many variations and modifications without departing from the spirit and scope of the invention. All such variations and modifications, including those discussed hereinabove, are intended to be included within the scope of the invention as defined in the appended claims.

We claim:

1. An electrode device adapted for use in medical devices, comprising a sheet of flexible fabric including a plurality of electrodes formed as part of said sheet, said sheet having inner and outer sides and being made from a plurality of yarns including first and second yarns, each of which is electrically non-conductive, and third yarns, each of which is electrically conductive, said first yarns extending in a first direction, said second and third yarns extending in a second direction which is different from said first direction, each of said third yarns including a plurality of segments exposed to said outer side of said sheet, said segments of said third yarns being arranged into groups, said segments of each of said groups being arranged side-by-side so as to form a corresponding one of said electrodes as part of said outer side of said sheet, each of said groups being separated from an adjacent one of said groups in said first direction by a set of said second yarns, and each of said groups being separated from an adjacent one of said groups in said second direction by a set of said first yarns.

2. The electrode device of claim 1, wherein said first yarns include a plurality of fill yarns, said second and third yarns including a plurality of warp yarns.

3. The electrode device of claim 1, wherein each of said first, second and third yarns is elastic so as to provide elasticity to said sheet.

4. The electrode device of claim 3, wherein each of said third yarns includes an electrically conductive strand, a reinforcement strand and an elastic strand, said conductive strand and said reinforcement strand of each of said third yarns being wound around a corresponding one of said elastic strands of said third yarns.

5. The electrode device of claim 4, wherein each of said first and second yarns includes an elastic strand and a reinforcement strand, said reinforcement strand of each of said first and second yarns being wound around a corresponding one of said elastic strands of said first and second yarns.

6. The electrode device of claim 1, wherein said sheet is formed into a first shape, said sheet being expandable from said first shape to a second shape, said sheet being contractible from said second shape to said first shape.

7. The electrode device of claim 6, further comprising expanding means for expanding said sheet from said first shape to said second shape.

8. The electrode device of claim 7, wherein said expanding means includes an expandable balloon, said sheet being attached to said balloon such that said sheet expands from said first shape to said second shape when fluid is injected into said balloon, said sheet contracting from said second shape to said first shape when the fluid is permitted to evacuate from said balloon.

9. A tissue ablation device comprising a sheet of flexible fabric including a plurality of electrodes formed as part of said sheet, said sheet having inner and outer sides and being made from a plurality of yarns including first and second yarns, each of which is electrically non-conductive, and third yarns, each of which is electrically conductive, said first yarns extending in a first direction, said second and third yarns extending in a second direction which is different from said first direction, each of said third yarns including a plurality of segments exposed to said outer side of said sheet, said segments of said third yarns being arranged into groups, said segments of each of said groups being arranged side-by-side so as to form a corresponding one of said electrodes as part of said outer side of said sheet, each of said groups being separated from an adjacent one of said groups in said first direction by a set of said second yarns, and each of said groups being separated from an adjacent one of said groups in said second direction by a set of said first yarns.

10. The tissue ablation device of claim 9, wherein said first yarns include a plurality of fill yarns; and wherein said second and third yarns include a plurality of warp yarns.

11. The tissue ablation device of claim 9, wherein each of said first, second and third yarns is elastic so as to provide elasticity to said sheet.

12. The tissue ablation device of claim 11, wherein each of said third yarns includes an electrically conductive strand, a reinforcement strand and an elastic strand, said conductive strand and said reinforcement strand of each of said third yarns being wound around a corresponding one of said elastic strands of said third yarns.

13. The tissue ablation device of claim 12, wherein each of said first and second yarns includes an elastic strand and a reinforcement strand, said reinforcement strand of each of said first and second yarns being wound around a corresponding one of said elastic strands of said first and second yarns.

14. The tissue ablation device of claim 11, wherein said sheet is formed into a first shape, said sheet being expandable from said first shape to a second shape, said sheet being contractible from said second shape to said first shape.

15. The tissue ablation device of claim 14, further comprising expanding means for expanding said sheet from said first shape to said second shape.

16. The tissue ablation device of claim 15, wherein said expanding means includes an expandable balloon, said sheet being attached to said balloon such that said sheet expands from said first shape to said second shape when fluid is injected into said balloon, said sheet contracting from said second shape to said first shape when the fluid is permitted to evacuate from said balloon.

* * * * *